(12) United States Patent
Brommersma

(10) Patent No.: US 7,955,329 B2
(45) Date of Patent: *Jun. 7, 2011

(54) UROLOGICAL RESECTOSCOPE FITTED WITH AN INSULATING ELEMENT AT ITS EXTERNAL STEM

(75) Inventor: Pieter Brommersma, Bargteheide (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/884,342

(22) Filed: Sep. 17, 2010

(65) Prior Publication Data
US 2011/0004055 A1 Jan. 6, 2011

Related U.S. Application Data

(62) Division of application No. 11/565,303, filed on Nov. 30, 2006, now Pat. No. 7,815,639.

(30) Foreign Application Priority Data

Dec. 2, 2005 (DE) .......................... 10 2005 057 933

(51) Int. Cl.
*A61B 18/14* (2006.01)
(52) U.S. Cl. .............................. 606/46; 606/45; 600/105
(58) Field of Classification Search .............. 606/45–47; 600/105
See application file for complete search history.

(56) References Cited

U.S. PATENT DOCUMENTS

| 3,973,568 | A | * | 8/1976 | Iglesias .......................... 606/46 |
| 4,726,370 | A | | 2/1988 | Karasawa et al. |
| 6,471,701 | B2 | * | 10/2002 | Brommersma et al. ........ 606/46 |
| 6,755,826 | B2 | * | 6/2004 | Valencic et al. ................ 606/46 |

FOREIGN PATENT DOCUMENTS

| DE | 3603758 A1 | 8/1986 |
| DE | 10122465 C1 | 8/2002 |

\* cited by examiner

*Primary Examiner* — Roy D Gibson
*Assistant Examiner* — Benjamin Lee
(74) *Attorney, Agent, or Firm* — Rankin, Hill & Clark LLP

(57) ABSTRACT

A urological resectoscope (1) includes a tubular, metallic external stem (2) fitted with holes (3) in its distal end zone, a tubular insulating element (7, 27, 37, 47) being affixed distally to the external stem, further comprising a tubular internal stem (8) configured within the external stem and resting against it in sealing manner and an electrode support (13) longitudinally displaceable inside the internal stem and supporting a cutting loop (15) in the region of the insulating element (7, 27, 37, 47), the inside space of the internal stem (8) and the gap (12) between the stems (2, 8) being proximally connected to liquid hookups (10, 11), the insulating element (7, 27, 37, 47) being configured in longitudinally mutually overlapping manner within an affixation zone (6) and the insulating element (7, 27, 37, 47) exhibiting a wall thickness distally from the affixation zone (6) larger than the wall thickness of the external stem (2), wherein the inside diameter of the insulating element (27, 47) is the same as the inside diameter of the external stem (2).

4 Claims, 1 Drawing Sheet

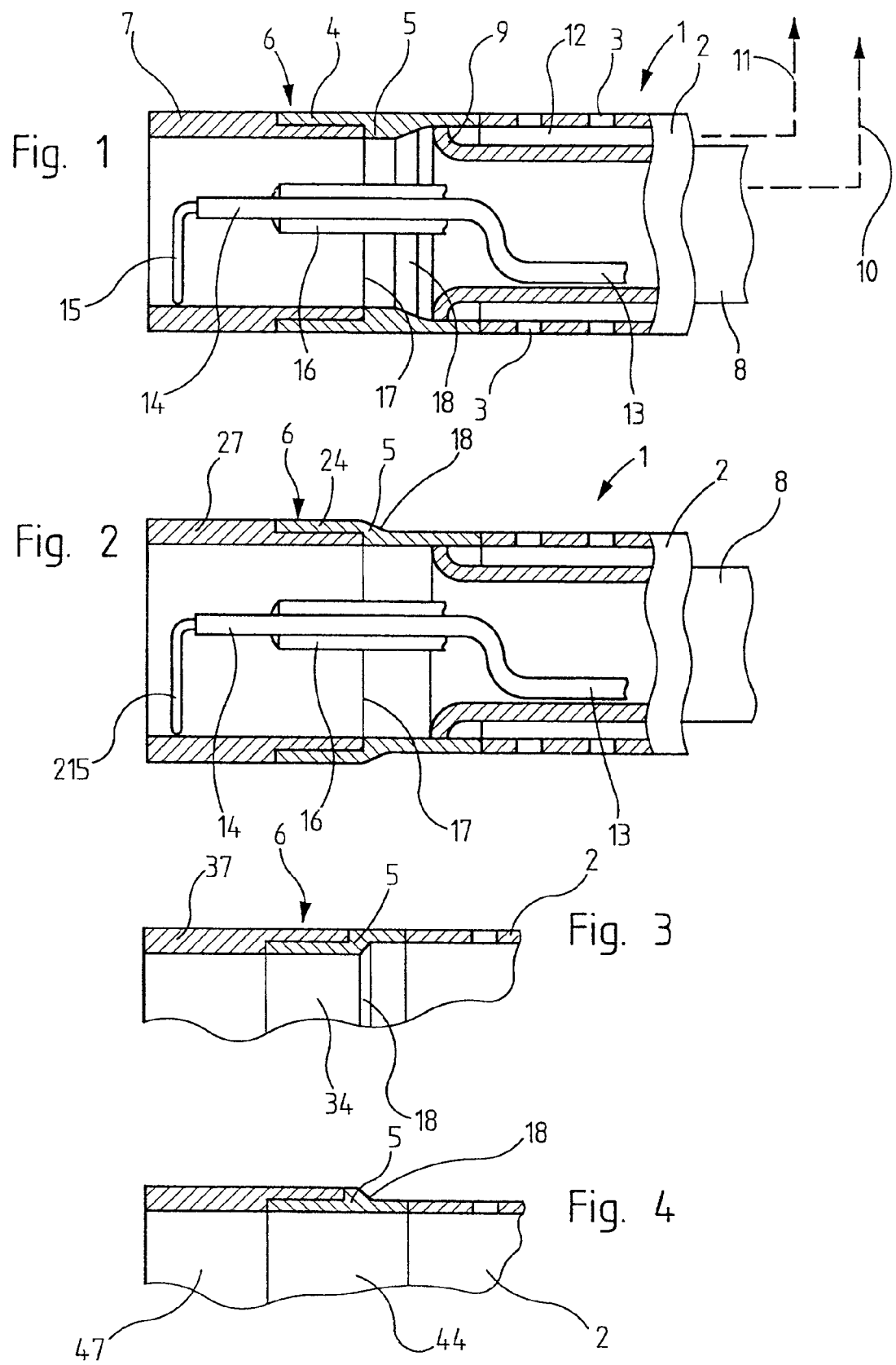

UROLOGICAL RESECTOSCOPE FITTED WITH AN INSULATING ELEMENT AT ITS EXTERNAL STEM

CROSS-REFERENCE TO RELATED APPLICATION

This application is a divisional application of U.S. patent application Ser. No. 11/565,303, entitled "UROLOGICAL RESECTOSCOPE FITTED WITH AN INSULATING ELEMENT AT ITS EXTERNAL STEM," which was filed on Nov. 30, 2006 now U.S. Pat. No. 7,815,639, the content of which is herein incorporated by reference.

BACKGROUND OF THE INVENTION

The insulating element of the stem of the present, state-of-the-art, standard urological resectoscope is affixed to the internal stem and, jointly with the latter, can be pulled out of the external stem in a proximal direction. Accordingly, the outside diameter of the insulating element must be smaller than the inside diameter of the external stem. Those insulating element outside-diameters that may still be tolerated by the patient therefore mandate a relatively narrow inside diameter of the insulating stem. On the other hand said insulating stem inside diameter determines the maximally feasible radius of the cutting loop. Yet, the cutting loop should be as large as possible to speed up resection.

A resectoscope, of the kind described, is known from the German patent document DE 101 22 465 C1. Therein the insulating element is affixed to the external stem and therefore may exhibit a larger inside diameter, making possible a larger cutting loop.

In such known resectoscope models, the insulating element's outside diameter corresponds to the external stem's outside diameter. The insulating element and the external stem are overlapping in their mutual affixation zone. As a result, the insulating element's inside diameter is smaller than that of the external stem. Again the size of the cutting loop is restricted.

The objective of the present invention is to create a urological resectoscope of the above kind that allows enlarging the cutting loop.

BRIEF SUMMARY OF THE INVENTION

In the present invention, the outer stem's inside diameter coincides with that of the insulating element. Accordingly, for a given external stem's outside diameter, the insulating element's inside diameter shall be larger than in the known designs and makes possible a larger cutting loop allowing speedier surgery. The insulating element's wall thickness being larger than that of the external stem, the design of the present invention provides an insulating element exhibiting a larger diameter than the external stem. However, this inherently interfering enlargement of the diameter is restricted to the short, distal longitudinal zone of the insulating element and does not significantly interfere when the external stem is inserted through a narrow body duct, for instance the urethra. Otherwise, the design of the present invention does not alter the design of the state of the art at the internal stem and at the other resectoscope components, and consequently such an external stem of the present invention together with its enlarged cutting loop can also be retrofitted onto resectoscopes of the state of the art.

Because of the last-mentioned feature, a resectoscope may be fitted with an external stem of the present invention and with a second external stem as disclosed in the patent document DE 101 22 465 C1. Both external stems may be selectively used with the same resectoscope, for instance the external stem of the present invention for a somewhat wider urethra wherein a large cutting loop is desirably used to cut a very large prostate, and the external stem of DE 101 22 465 C1 wherein the insulating element's outside diameter corresponds to that of the external stem where a very narrow urethra is involved.

As regards the external stem of the present invention, the insulating element projects outward beyond the external stem, resulting in an interfering edge when the external stem is pulled out of the patient's body. As regards an external stem of which the outside diameter coincides with that of the insulating element, this insulating element projects inward and there constitutes an edge. This edge interferes when the external stem is slipped over the internal stem and the cutting loop because said edge may damage the cutting loop. These interfering edges can be dulled. The external stem subtends a beveled bulge at the edge whereby the insulating element projects outward or inward beyond the external stem, such beveling precluding injury to human tissue or damage to the cutting loop.

The external stem zone overlaps, in affixing manner, the insulating element and the bulging external stem zone is constituted at a cross-sectionally contoured annulus affixed to the external stem in appropriate manner, for instance by fusion or bonding. As a result the manufacture of the complex, cross-sectionally contoured annulus shall be simplified in said zone because of being separately manufacturable, for instance on a lathe.

BRIEF DESCRIPTION OF THE DRAWINGS

The present invention is shown schematically and in illustrative manner in the appended drawings.

FIG. 1 is a section of the tip zone of a resectoscope of a design substantially corresponding to that of the German patent document DE 101 22 465 C1, FIG. 2 is a section corresponding to FIG. 1 of a resectoscope of the invention, FIG. 3 is a partial cutaway of a design variation of FIG. 1, and FIG. 4 is a partial cutaway of a design variation of FIG. 2.

DETAILED DESCRIPTION OF THE INVENTION

FIG. 1 shows the tip zone of an urological resectoscope 1 of a design substantially that of the German patent document DE 101 22 465 C1. An external stem 2 is fitted at its distal end region with holes 3. The distal end element of the external stem 1 is designed illustratively as a cross-sectionally contoured annulus 4 affixed by a fusion seam and fitted with an inward bulge 5. At its affixation portion 6, the cross-sectionally contoured annulus 4 overlaps an insulating element 7 which in said portion exhibits a reduced outside diameter. The external stem 2 and the insulating element 7 are tubular. Illustratively, the insulating element 7 is made of a ceramic whereas the external stem 2 and the cross-sectionally contoured annulus 4 is made of metal.

An annular internal stem 8 is mounted within the external stem 2 and at its distal end rests in sealing manner by means of a flaring element 9 against the external stem 2, i.e. against the cross-sectionally contoured annulus 4.

The external stem 2 and the internal stem 8 are joined to an end segment at the omitted proximal stem end region, at least the external stem, and possibly the internal stem 8, being detachable.

Liquid hookups are present in the proximal end region, one liquid hookup 10 feeding liquid to the inside of the internal stem 8 and another liquid hookup 11 draining liquid from the gap 12 between the internal stem 8 and the external stem 2. In this manner, continuous rinsing is implemented in the region in front of the distal stem end, the liquid being continuously supplied from the internal stem being drained through the holes 3 and the gap 12.

An electrode support 13 is mounted inside the internal stem 8 and branches into fork arms 14 in the distal end zone, a cutting loop 15 of conventional design being configured between said fork arms' distal ends. Said loop makes contact, at the omitted distal end of the electrode support 13, with a high-frequency source and can be driven longitudinally in a controlled manner from its proximal end to perform surgery.

Also, an optics 16 is configured inside the internal stem 8 to look through its distal objective lens at the surgery space.

The external stem 2 shown in FIG. 1 might be fitted with a smooth inside diameter as far as the overlap zone of the affixation portion 6 and may be directly affixed there by bonding, soldering or the like on the diameter-reducing segment of the insulating element 7. In that case, however, an inwardly projecting and possibly interfering edge would be created at the proximal end of said insulating element.

When using the shown resectoscope, frequently the entire sub-assembly present within the external stem 2 must be proximally withdrawn from this stem for instance to eliminate clogging in the gap 12 or to exchange the cutting loop 15. In the process, however, the outer stem should remain in the human body, for instance in the urethra, in order to preclude additional damage caused by continual withdrawal and re-insertion. Illustratively, the cutting loop 15 being re-inserted might be damaged at the inwardly projecting insulating element end 17.

Accordingly the design of FIG. 1 is advantageous, whereby a bulge 5 is provided at the outer stem 2, 4, said bulge covering inwardly the end 17 of the insulating element 7 and by means of a beveled transition 18 allowing non-damaging insertion of the cutting loop 15. Moreover, the design of the distal end zone of the external stem 2 as an attached cross-sectionally contoured annulus 4 allows for more easily manufacturing/processing it for instance using a lathe.

FIG. 2 shows a design of the invention, which differs from that of FIG. 1, where the same reference symbols and the same sizes are used as much as possible.

The external stem 2 and the internal stem 8, as well as the optics 16 and the electrode support 13 of the invention, are entirely identical with those of FIG. 1. The length of the insulating element 27 is also the same.

However, contrary to the design of FIG. 1, while keeping the wall thickness of the insulating element 27 unchanged, its diameter is now enlarged in a manner that its inside diameter coincides with the inside diameter of the external stem 2 as shown in FIG. 2. As a result and as shown by comparing FIGS. 1 and 2, the cutting loop 215 of FIG. 2 is substantially larger than in FIG. 1 while the remaining design is the same.

In the design of the invention shown in FIG. 2, the outside diameter of the insulating element 27 is larger than the outside diameter of the external stem 2. Accordingly, an edge is generated at the proximal edge 17. The sharpness of this edge is dulled again by the bulge 5 of the cross-sectionally contoured annulus 24 by means of the beveled transition 18, the bulge 5 in the design of FIG. 2 protruding outward instead of inward as in the design of FIG. 1.

FIG. 3 shows a design variation of FIG. 1, where the affixation zone 6 of the external stem 2 does not overlap externally the insulating element 37 as shown in FIG. 1, but instead overlaps it internally. The distal end zone of the external stem 2 again is a cross-sectionally contoured annulus 34 with a bulge 5 and a beveled transition 18 exhibiting the above cited features to protect the cutting loop 15 against damage.

FIG. 4 shows a similar design variation with respect to FIG. 2, again the external stem 2 overlapping from inside the insulating element 47. Again, the cross-sectionally contoured annulus 44 comprises a bulge 5 constituting the beveled transition 18.

Other, omitted embodiment variations of the affixation segment 6 are conceivable, illustratively in one instance eliminating the cross-sectionally contoured annulus, where the joined stem parts are then affixed to each other in butting manner without overlap.

Comparison of FIGS. 1 and 2 indicates that the differences between the two designs are restricted to the region of the insulating element 7, 27 and to the size of the cutting loop 15, 215; otherwise all components are the same; accordingly the external stem of FIG. 2 is exchangeable in a problem-free manner with that of FIG. 1, requiring, however, an exchange of electrode supports with different cutting loops. Consequently a resectoscope may be advantageously outfitted with two external stems, one as shown in FIG. 1 and one as shown in FIG. 2, which shall be used alternatively as needed with a corresponding cutting loop.

The invention claimed is:

1. A urological resectoscope comprising:
 a tubular, metallic external stem fitted with holes in its distal end zone,
 a tubular insulating element being affixed distally to said external stem,
 a tubular internal stem configured within said external stem and resting distally against said external stem in a sealing manner, and
 an electrode support longitudinally displaceable inside said internal stem and supporting a cutting loop in the region of the insulating element,
 wherein the inside space of the internal stem and the gap between the stems is proximally connected to liquid hookups,
 wherein the internal stem and the electrode support are connected to the outer stem in a manner allowing the internal stem and the electrode support to be proximally pulled out of the external stem,
 wherein the external stem and the insulating element are configured in a longitudinally mutually overlapping manner within an affixation zone,
 wherein the external stem bulges in the region directly proximal to the affixation zone in the form of a beveled transition increasing in width obliquely and distally to the wall thickness of the insulating element and wherein the thickness of the external stem varies in this region,
 wherein the insulating element exhibits a wall thickness distally from the affixation zone larger than the wall thickness of the external stem, and
 wherein the outside diameter of the insulating element is the same as the outside diameter of the external stem.

2. The resectoscope as claimed in claim 1, wherein the resectoscope further comprises a second, exchangeable external stem having the same inside diameter as the first external stem, wherein the insulating element has the same inside diameter as the second external stem, the two external stems forming a resectoscope kit.

3. The resectoscope as claimed in claim 1, wherein the zone overlapping the insulating element and the bulging zone of the external stem is constituted by a cross-sectionally contoured annulus affixed to said external stem.

4. The resectoscope as claimed in claim 1, wherein the external stem is single-walled.

* * * * *